United States Patent [19]

Smith et al.

[11] 4,309,505

[45] Jan. 5, 1982

[54] PROCESS FOR THE PRODUCTION OF FRUCTOSE TRANSFERASE ENZYME

[75] Inventors: Jay A. Smith, Downers Grove; Susan J. Luenser, LaGrange Park, both of Ill.

[73] Assignee: CPC International Inc., Englewood Cliffs, N.J.

[21] Appl. No.: 150,843

[22] Filed: May 19, 1980

[51] Int. Cl.³ ............................................... C12N 9/10
[52] U.S. Cl. .................................... 435/193; 435/255; 435/911
[58] Field of Search ........................ 435/193, 911, 255

[56] References Cited

U.S. PATENT DOCUMENTS 4,276,379 6/1981 Heady .............................. 435/193 X Primary Examiner—Lionel M. Shapiro
Attorney, Agent, or Firm—Stanley M. Parmerter

[57] ABSTRACT

An improved process for obtaining fructosyl transferase enzyme from the yeast *Aureobasidium pullulans*. Prior purification process steps are eliminated by use of conditions which do not produce black pigments and viscous polysaccharides.

9 Claims, No Drawings

PROCESS FOR THE PRODUCTION OF FRUCTOSE TRANSFERASE ENZYME

FIELD OF THE INVENTION

This invention relates to an improved process for the production of fructosyl transferase enzyme by the black yeast *Aureobasidium pullulans*.

BACKGROUND OF THE INVENTION

Because fructose is sweeter than either glucose or sucrose, much effort has gone into developing processes for producing syrups in which more than 50% of the carbohydrate is fructose. Recently, a novel way to obtain fructose syrup of greater than 50% fructose content was disclosed in British Pat. No. 2,000,144. According to that procedure, a sucrose substrate is subjected to the action of a fructosyl transferase enzyme to convert the sucrose to an intermediate syrup containing predominantly fructose polymers and glucose. This syrup, in which the fructose is in polymeric form, can be further treated to produce fructose syrups in which more than 50% of the carbohydrate is fructose. An economical source of fructosyl transferase enzyme is essential to the successful operation of this process.

British Pat. No. 2,000,144 describes a process for the production and isolation of a fructosyl transferase enzyme from the fermentation broth of *Aureobasidium pullulans*. However, the fermentation carried out according to the process of that disclosure produces a black, viscous broth which contains large amounts of the polysaccharide, pullulan. Extensive processing is necessary to remove the color and the pullulan before the fructosyl transferase enzyme can be isolated. Furthermore, the amount of enzyme obtained from the fermentation broth is comparatively low. There, therefore, exists a need for an improved process for the production of a fructosyl transferase enzyme preparation.

SUMMARY OF THE INVENTION

In accordance with the present invention, there is provided an improved process for the production of fructosyl transferase enzyme. This process involves inoculating a culture medium with cells from a strain of *Aureobasidium pullulans*. The culture medium contains about 16 to about 24% weight by volume (w/v of sucrose, about 1 to about 2.4% (w/v) yeast extract or its nutrient equivalent, and about 1% (w/v) of an inorganic nitrate salt. The mixture is cultured at a pH of between 6 to 8 at a temperature of from 28° to 32° C. until a yield of fructosyl transferase enzyme is obtained. The enzyme preparation is then recovered from the culture medium.

DETAILED DESCRIPTION OF THE INVENTION

For the purposes of this specification, the following definitions are provided for the various terms used herein:

1. Enzyme Preparation

The term "enzyme preparation" is used herein to refer to any composition of matter which exhibits the desired enzymatic activity. The term is used to refer, for example, to cell extracts, refined and concentrated preparations derived from the cells and from culture liquors. The enzyme preparation may also include a composition in which the enzyme is bound to or absorbed on an inert carrier.

2. Fructosyl Transferase Enzyme

As used herein, this term refers to any enzyme that catalyzes the transfer of a fructosyl group from a donor, e.g., sucrose, to an acceptor. It includes the enzyme preparation derived from *Aureobasidium pullulans*, ATCC No. 9348 (synonymous with *Pullularia pullulans*).

3. Fructosyl Transferase Unit

As used herein, one fructosyl transferase unit is defined as the amount of enzyme activity required to produce one micromole or reducing sugar, calculated as flucose, per minute under the following conditions: (a) pH 5.5, (b) temperature 55° C., and (c) substrate concentration at 60 g food-grade sucrose per 100 ml of an aqueous reaction mixture.

Reducing sugar (calculated as glucose) can be determined using a "Technicon Autoanalyzer II" (Technicon, Inc., Tarrytown, New York). Analysis is carried out by a conventional alkaline ferricyanide method, *Analytical Biochemistry* 45, No. 2, pp. 517–524 (1972), adapted for use in the "Autoanalyzer II". Unless otherwise designated, enzyme activity determinations are performed by continual monitoring of a reaction mixture consisting of the following composition:

7.5 ml of 80% (w/v) aqueous food-grade sucrose solution.

2.3 ml 0.1 M citrate buffer pH 5.5.

0.2 ml enzyme sample containing that amount of fructosyl. transferase enzyme which will produce from 5–25 micrograms of reducing sugar (calculated as glucose) per minute per ml of reaction mixture.

Any strain of *Aureobasidium pullulans* capable of producing a fructosyl transferase enzyme can be employed in the process of this invention. Suitable strains of this yeast include NRRL No. 3937, ATCC No. 12535, NRRL No. 1673, NRRL No. Y 2311, NRRL No. YB 3892, ATCC No. 15223, and NRRL No. YB 3861. A particularly suitable strain is ATCC No. 9348.

The process of this invention employs conventional fermentation equipment and procedures. Generally, the yeast culture is maintained or preserved on agar slants with periodic transfer to maintain viability. In the inoculum development, the culture is transferred from the slant to a liquid culture medium in order to provide an active culture in sufficient volume to inoculate the final production medium. The inoculum development stage may consist of a single transfer to a liquid medium or may include several successive transfers as required to provide for activation of the culture or to build sufficient volume for inoculation of a final production medium. It is in the final production medium where the desired enzyme is produced for use, either directly or after further processing or purification.

The improved fructosyl transferase enzyme yields obtained by this process are due to part to the use of a more concentrated sucrose solution as a carbohydrate source for the growth of the microorganism. Increased yields of fructosyl transferase enzyme are obtained by the use of culture medium containing from about 16% to about 24% (w/v) sucrose in the medium. A preferred range of sucrose concentration is from about 20% to about 24% (w/v). Higher concentrations of sucrose fail to give appreciably enhanced yields of the enzyme.

The improved yields of fructosyl transferase enzyme obtained by the process of this invention are also due in part to the use of increased concentrations of yeast extract in the medium. Suitable concentrations of yeast extract are from about 1% to about 2% (w/v). A preferred concentration of yeast extract is about 2.0% (w/v). A suitable yeast extract is that available from Difco Laboratories, Inc., Detroit, Michigan. Other preparations which are the nutrient equivalent of yeast extract may be substituted for this ingredient. For example, Amber BYF 50X, a pure autolyzed brewers' yeast fraction available from the Amber Laboratories, Juneau, Wisconsin, may be used at a concentration of from about 5% to about 10% (w/v) in place of the yeast extract.

For the most successful preparation of fructosyl transferase enzyme by the process of this invention, a water-soluble, inorganic nitrate salt is also added to the culture medium in which the cells of *Aureobasidium pullulans* are grown. Any of the common nitrate salts, such as sodium nitrate, are suitable. A preferred concentration of the salt is about 1% (w/v).

The pH of the culture medium used in the process of this invention is adjusted to between 6 and 7 and the medium is sterilized by heating for from ½ to 2 hours at 120° C. before it is inoculated with the cell culture. The pH of the culture medium is maintained between 6.0 and 8.0 during the course of the fermentation by the addition of dilute acid or base as necessary. A preferred range for the fermentation is from about 6.5 to about 7.5. When the fermentation medium of this invention was employed, the pH of the medium tended to increase or hold constant rather than decrease as had been the case with the fermentations of the prior art process.

Another unexpected result of the use of the fermentation medium of this invention was the discovery that the black pigment formed in the prior art fermentations was not obtained. This avoided the inconvenience and expense of a separate precipitation step to remove this pigment before the enzyme could be isolated.

A further unexpeted benefit was derived from the process of this invention. It was discovered that almost none of the viscous polysaccharide, pullulan, was produced. In the prior art process, a costly and time-consuming step was required to remove this high molecular weight product before the enzyme could be separated. Since the removal of this product and the precipitation of the black pigment are no longer necessary, enzyme isolation is greatly simplified.

The fermentation process of this invention is conveniently carried out at a temperature of from about 28° C. to about 32° C. A preferred temperature range is from about 30° C. to about 31° C. Although the fermentation can be carried out below 28° C. and above 32° C., the yield of fructosyl transferase enzyme produced when the fermentation is carried out in those temperature ranges is substantially lower than that obtained when the fermentation is run at temperatures between 28° C. and 32° C.

A satisfactory yield of fructosyl transferase enzyme is usually present after the fermentation has been carried out for approximately 100 hours. However, the optimum time for the fermentation varies somewhat depending on the exact temperature used as well as on the concentration of the nutrient materials employed.

In this new process, over 80% of the furctosyl transferase enzyme is present in the broth. This contrasts with the prior art fermentation wherein nearly half of the enzyme was cell-bound. Because the bulk of the enzyme is now present in the broth, a simple enzyme recovery process is feasible.

A fructosyl transferase enzyme preparation suitable for many applications can be obtained by simply removing the yeast cells from the fermentation mixture. This separation can be accomplished by any of the conventional means, such as centrifugation or filtration. The enzyme solution can be concentrated, if desired, by evaporation at temperatures below those which cause inactivation of the enzyme. This is conveniently carried out in a rotary vacuum evaporator at temperatures below 50° C.

If a solid enzyme preparation is desired, the enzyme can be adsorbed on diatomaceous earth. This is accomplished by simply adding the diatomaceous earth to the cell-free fermentation broth. Addition of a water-soluble organic solvent, such as 2-propanol or acetone, causes the enzyme to precipitate and be adsorbed on the diatomaceous earth. The composite of diatomaceous earth and fructosyl transferase enzyme is then isolated by filtration or centrifugation.

The procedure of this invention is further illustrated by the following examples in which all parts are by weight and all percentages are weight by volume (w/v) unless expressly stated to be otherwise.

EXAMPLE 1

The medium used for inoculum development is as follows:
0.5% Dibasic Potassium Phosphate
0.1% Sodium Chloride
0.02% Magnesium Sulfate.Heptahydrate
0.06% Ammonium Nitrate
0.3% Yeast Extract (Difco Laboratories)
6% Sucrose
pH of medium adjusted to 6.8

The seed flasks, 500-ml Erlenmeyer's containing 100 ml of sterile medium, are inoculated from a slant culture of the black yeast, *Aureobasidium pullulans*. The particular strain of the yeast employed was designated in the catalogue of the American Type Culture Collection (Rockville, Maryland) as ATCC No. 9348. The seed flasks, after development on a reciprocal shaker for 48 hours at 30° C., were used to inoculate second-stage seed flasks. Five milliliters of the inoculum from the first seed flask was added to 100 ml of fresh sterile medium in a second 500-ml Erlenmeyer seed flask. The second seed flasks were developed on a reciprocal shaker for 24 hours at 30° C. before the entire contents of one flask was used to inoculate 4 liters of sterile medium in a 7.5-liter fermentor. The media used for the various runs is given in the following table:

TABLE I

| | FERMENTATION MEDIA Composition, % Weight/Volume | | | | |
| --- | --- | --- | --- | --- | --- |
| | Run No. | | | | |
| Component | 1 | 2 | 3 | 4 | 5 |
| $K_2HPO_4$ | 0.5 | 0.5 | 0.5 | 0.5 | 0.5 |
| $MgSO_4 \cdot 7H_2O$ | 0.05 | 0.05 | 0.05 | 0.05 | 0.05 |
| $NaNO_3$ | 1.0 | 1.0 | 1.0 | 1.0 | 1.0 |
| Yeast Extract (Difco Labs.) | 2.0 | 2.4 | 2.4 | 2.0 | — |
| Amber BYF 50X (Amber Labs.) | — | — | — | — | 8.0 |
| Sucrose | 20 | 24 | 20 | 20 | 20 |
| Antifoam[a] | 0.025 | 0.025 | 0.025 | 0.025 | 0.025 |

[a]The antifoam agent was polypropylene glycol, mol. wt. 2000.

In each run, the pH was adjusted to 6.5 before inoculation from the seed flasks. Runs Nos. 1, 2 and 3 were made at 30°–31° C. Runs Nos. 4 and 5 were made at 33°–34° C. The fermentations were carried out with an agitator speed of 580 rpm and with 4 liters of air per minute passing through the mixture. It was necessary to add 75 ml of 2 N HCl to Run No. 4 after 27 hours to reduce the pH from 7.5 to 6.5. After 50 hours, an additional 30 ml of 2 N HCl was added to Run No 4 to reduce the pH from 7.5 to 6.5. At periodic intervals, samples were removed from the fermentor, the broth was separated from the cells by centrifugation and analyzed for fructosyl transferase enzyme activity. The results of these analyses are given in Table II.

TABLE II

FRUCTOSYL TRANSFERASE ENZYME PRODUCTION
Units/ml in Broth

| Time | Run No. | | | | |
|---|---|---|---|---|---|
| (hrs) | 1 | 2 | 3 | 4 | 5 |
| 27 | 77 | 58 | 56 | 59 | 39 |
| 42 | 145 | 126 | 123 | 79 | 88 |
| 50 | 178 | 171 | 158 | 81 | 106 |
| 66 | 238 | 234 | 221 | 104 | 144 |
| 90 | 290 | 355 | 302 | 144[a] | 159[a] |
| 114 | 440 | 438 | 380 | — | — |

[a]The fermentation was stopped after 90 hours when the medium became very black.

These results show that fermentations run above 33° C. (Runs Nos. 4 and 5) are much less satisfactory for the production of fructosyl transferase enzyme than the runs at 30°–31° C. These results further show that neither increasing the sucrose concentration in the medium above 20% (Run No. 2) nor increasing the yeast extract concentration in the medium above 2% (Runs Nos. 2 and 3) increases the production of fructosyl transferase enzyme in the fermentation. A comparison of Runs Nos. 4 and 5 shows that an alternate nutrient supply can be substituted for yeast extract in the fermentation.

COMPARATIVE TEST 1

(Prior Art Process)

Inoculum development was carried out as in Example 1. The entire contents of one second-stage seed flask was used to inoculate 4 liters of sterile medium in a 7.5-liter fermentor. The medium used had the following composition:

0.5% Dibasic Potassium Phosphate
0.1% Sodium Chloride
0.02% Magnesium Sulfate.Heptahydrate
0.06% Ammonium Nitrate
0.3% Yeast Extract (Difco Laboratories)
12% Sucrose
0.025% Propylene Glucol, mol. wt. 2000

The pH of the medium was adjusted to 6.8 before inoculation from the seed flasks. The fermentation was carried out at 30° C. with an agitator speed of 500 rpm and with 4 liters of air per minute passing through the mixture. The pH of the mixture dropped to 4.2 after 32.5 hours and remained at 4.2±0.1 throughout the rest of the reaction. At periodic intervals, samples were removed from the fermentor, the broth was separated from the cells by centrifugation and analyzed for fructosyl transferase enzyme activity. The results of these analyses are as follows:

FRUCTOSYL TRANSFERASE ENZYME PRODUCTION

| Time (hrs) | Units/ml in Broth |
|---|---|
| 19 | 19.5 |
| 25.5 | 26.2 |
| 43 | 31.7 |
| 67 | 40.6 |
| 72 | 47.6 |
| 90 | 49.7 |
| 150 | 53.4 |

The reaction mixture was very black. This comparative test illustrates the comparatively low enzyme yields and highly pigmented reaction mixtures that were obtained by the prior art process.

What is claimed is:

1. An improved process for producing a fructosyl transferase enzyme preparation which comprises: inoculating a culture medium with cells from a strain of *Aureobasidium pullulans,* said culture medium comprising about 16 to about 24% (w/v) sucrose, about 1 to about 2.4% (w/v) yeast extract and about 1% (w/v) of an inorganic nitrate salt; and culturing the mixture at a pH of between 6 and 8 at 28°–32° C. until a yield of fructosyl transferase enzyme is obtained, wherein the enzyme preparation is recovered in high yields from the culture medium without the need to remove any black pigment or viscous polysacchride.

2. The process of claim 1 wherein the sucrose concentration is 20–24% (w/v).

3. The process of claim 1 wherein the yeast extract is about 2% (w/v).

4. The process of claim 1 wherein the pH of the culture mixture is maintained at between 6.5 and 7.5.

5. The process of claim 1 wherein the culture medium is maintained at a temperature of between 30° and 31° C.

6. The process of claim 1 wherein the concentration of sucrose in the culture medium is about 20% (w/v), the concentration of yeast extract is about 2% (w/v), the pH of the mixture is maintained between 6.5 and 7.5 and the temperature of the culture medium is maintained at 30°–31° C.

7. The process of claim 1 wherein about 5 to about 10% (w/v) Amber BYF 50X is used in place of the yeast extract.

8. The process of claim 1 further characterized in that the culture medium is freed from cells by centrifugation before a portion of the liquid is evaporated to give a concentrated fructosyl transferase enzyme preparation.

9. The process of claim 1 which further comprises centrifuging the culture medium to remove yeast cells, adding diatomaceous earth to the cell-free liquid, precipitating the enzyme on the diatomaceous earth by the addition of a water-soluble organic solvent and separating the enzyme-containing solid.

* * * * *